(12) United States Patent
Kim

(10) Patent No.: US 6,780,802 B2
(45) Date of Patent: Aug. 24, 2004

(54) FAR INFRARED RADIOACTIVE GLASS PRODUCTS FOR LIGHTING AND MANUFACTURING METHODS THEREFOR

(76) Inventor: Jong-Wook Kim, 401, 1 008-12, Sadang 1-dong, Tongjak-gu, Seoul (KR), 156-824

( * ) Notice: Subject to any disclaimer, the term of this patent is extended or adjusted under 35 U.S.C. 154(b) by 99 days.

(21) Appl. No.: 10/257,807

(22) PCT Filed: Feb. 20, 2001

(86) PCT No.: PCT/KR01/00249

§ 371 (c)(1),
(2), (4) Date: Oct. 15, 2002

(87) PCT Pub. No.: WO01/79129

PCT Pub. Date: Oct. 25, 2001

(65) Prior Publication Data

US 2003/0133296 A1 Jul. 17, 2003

(30) Foreign Application Priority Data

Apr. 19, 2000 (KR) .......................................... 2000-11129
Apr. 19, 2000 (KR) .......................................... 2000-20724
Sep. 18, 2000 (KR) .......................................... 2000-54682

(51) Int. Cl.$^7$ ............................ C03C 6/02; C03C 14/00
(52) U.S. Cl. ............................... 501/27; 501/32; 501/70
(58) Field of Search .............................. 501/17, 21, 27, 501/32, 70

(56) References Cited

FOREIGN PATENT DOCUMENTS

| JP | 10-88103 | 4/1998 |
| JP | 10-219139 | 8/1998 |
| JP | 11-84233 | 3/1999 |
| KR | 91-15930 | 9/1991 |
| KR | 94-1707 | 1/1994 |
| KR | 95-27988 | 10/1995 |

*Primary Examiner*—Karl Group
*Assistant Examiner*—Elizabeth A. Bolden
(74) *Attorney, Agent, or Firm*—Merchant & Gould P.C.

(57) ABSTRACT

The invention relates to an illuminating glass product having far infrared ray radiation in which far infrared ray radiating glass is made of use for an illuminating bulb or a glass diffuser for illumination and emission of far infrared rays at the same time.

2 Claims, 2 Drawing Sheets

FAR INFRARED RADIOACTIVE GLASS PRODUCTS FOR LIGHTING AND MANUFACTURING METHODS THEREFOR

TECHNICAL FIELD

The present invention relates to an illuminating glass product having far infrared ray radiating capability, and more particularly to an illuminating glass product in which far infrared ray radiating glass is applied to an illuminating bulbs or glass diffusers for simultaneous illumination and radiation of far infrared ray.

BACKGROUND OF THE INVENTION

In general, all materials existing on earth emit electronic waves corresponding to a temperature higher than an absolute temperature of (−273 centigrade degrees). Electronic waves existing within the wavelength range of 0.76–1000 $\mu$m are called far infrared ray. On the other hand, all living creatures consisting of organic chemical compounds have a unique absorption wavelength range of 4–15 $\mu$m which falls in the wavelength range of far infrared ray, and particularly, the far infrared ray falling at the wavelength range of 4–15 $\mu$m has been already proven to be beneficial to living bodies to thereby bring about an increase in social attention to far infrared ray.

If far infrared ray radiates to water molecules that consist of cells in a human body, it vibrates the body cells minutely over 2000 times per minute to activate the cell tissues and invigorate their life cycle. Thus, such cell activities result in natural effects of generating heat energy and eliminating waste matters from the body cells.

A further detailed description will be made about biodynamics of the far infrared ray below. All materials consist of molecules, each of which is made up of atoms. The atoms bring about a molecular motion at over an absolute degree of zero (−273 centigrade degree). At this time, the cycle of a molecular motion is determined by mass and alignment of atoms and the whole shape of a molecule. According to the vibration theory, the radiation of electronic waves of a frequency identical to a unique vibration frequency of a molecule will result in resonance which enlarges the amplitude of vibrations and raise the internal temperature of a material. According to the vibration theory as such, if far infrared ray is radiated to water molecules and cells or tissues of the living bodies (agricultural and marine products), it will activate resonance to stimulate metabolism and enhance growth of the living creatures.

Particularly, a water molecule is made up of two hydrogen atoms forming an angle of 104° 31' at the center of one oxygen atom with 4 types of motions such as deflective motion, translational motion, rotational motion, expansion and shrinkage motion, and the water molecule has its self-vibrational wavelength range of 6–11 $\mu$m. When a far infrared ray with the same wavelength range is radiated, the water molecule is activated by resonance to reinforce its performances inside the body. For instance, all the enzymes related to various metabolisms of living organisms are contained in water, activation of the water molecules resultantly stimulates the enzymes of living bodies to smoothly boost up metabolism in the body. Besides, the body tissue has a large absorption of long waves at the wavelength range of far infrared ray, over 7 $\mu$m, so that the tissue will easily absorb the long waves to activate water molecules if far infrared ray is radiated.

However, at present, most buildings constructed with cement or daily commodities made of chemical raw materials often block radiation of such far infrared rays beneficial to living creatures. Therefore, more efforts start to be exerted to develop a variety of daily goods that can make an effective use of well known benefits of such far infrared rays for such construction materials as wall paper, floor paper and other various thermal treatment devices made of far infrared ray radiating materials.

A variety of daily goods radiating far infrared rays are made of ceramics, granite porphyry, rough germanium stones which are used as they are, grounded in powder or mixed with other additives into solid products. However, among such products, a decorative goods or wall paper is not equipped with heating means to result in a poor far infrared ray radiating effect. On the other hand, a heating mat also requires an additional heating means to bring about an increase in the manufacturing cost and an inconvenience in use.

Furthermore, the conventional far infrared ray radiating goods themselves tend to absorb or reflect light which falls under a wavelength range of 3–15 $\mu$m, the most beneficial to living bodies, so as to keep the far infrared rays from radiating to targeted areas. As a result, it has been difficult to expect the conventional far infrared ray radiating goods to make beneficial effects onto living bodies.

The inventor has recognized the aforementioned disadvantages and developed the present invention by applying a fact that a lightening apparatus is selected the most adequate to maximize the far infrared ray radiating effects to living bodies and made into a daily goods that can generate heat with a filament and keep itself close to living bodies for a long period of time every day.

SUMMARY OF THE INVENTION

It is an object of the present invention to provide an illuminating glass product made with far infrared ray radiating glass containing a far infrared ray radiating substance (A).

It is another object of the present invention to provide an illuminating glass product including a bulb or a glass diffuser.

It is a third object of the present invention to provide an illuminating glass product mainly made up of silicon-dioxide, soda lime, lime stone, aluminum hydroxide, potassium carbonate powder as far infrared ray radiating glass.

It is a fourth object of the present invention to provide an illuminating glass product made up of nephrite having chemical structure of $Ca_2(Mg,Fe)_5Si_8O_{22}(OH)_2$ as a far infrared ray radiating matter (A).

It is a fifth object of the present invention to provide an illuminating glass productmade of far infrared ray radiating glass in which a previously manufactured glass plate is coated into a layer with the a far infrared ray radiating matter (A).

It is a sixth object of the present invention to provide an illuminating glass product made up of powdered nephrite, a far infrared ray radiating matter (A), and a glass component material (B) at the mixing ratio (weight percentage) of 10–1:90–99.

It is a seventh object of the present invention to provide a method for manufacturing an illuminating glass product having a far infrared ray radiating function, comprising the steps of:

mixing and stirring the 90–99 percents in weight of glass material powder like silicon-dioxide, soda lime, lime stone, aluminum hydroxide or potassium carbonate and the 10–1 percent in weight of nephrite powder indicated with the chemical structure of $Ca_2(Mg,Fe)_5Si_8O_{22}(OH)_2$;

liquefying the powder mixture at the temperature of 1300 through 1350 centigrade degrees; and cooling off the liquid mixture in a mold into a predetermined shape of an illuminating glass product.

It is an eighth object of the present invention to provide another method for manufacturing an illuminating glass product, comprising the steps of:

finely grinding nephrite, indicated with the chemical structure of $Ca_2(Mg,Fe)_5Si_8O_{22}(OH)_2$;

mixing the nephrite powder into a pigment;

coating the mixture onto a pre-manufactured glass plate in a silk printing method with a silk mesh;

drying the glass plate; and solidifying it with an electric heater.

The present invention relates to an illuminating device having a glass product.

In the present invention, an illuminating glass product is provided to be used for cattle pens, pig pens, fish-farming houses, aquariums, crop growing facilities, medical treatments, hair salons, saunas or fermented food ripening facilities.

The present invention provides a Braun tube for cathode ray tube (CRT) monitoring made of illuminating glass.

BRIEF DESCRIPTION OF THE DRAWINGS

For fuller understanding of the nature and object of the invention, reference should be made to the following detailed description taken in conjunction with the accompanying drawings in which.

Figure 1:
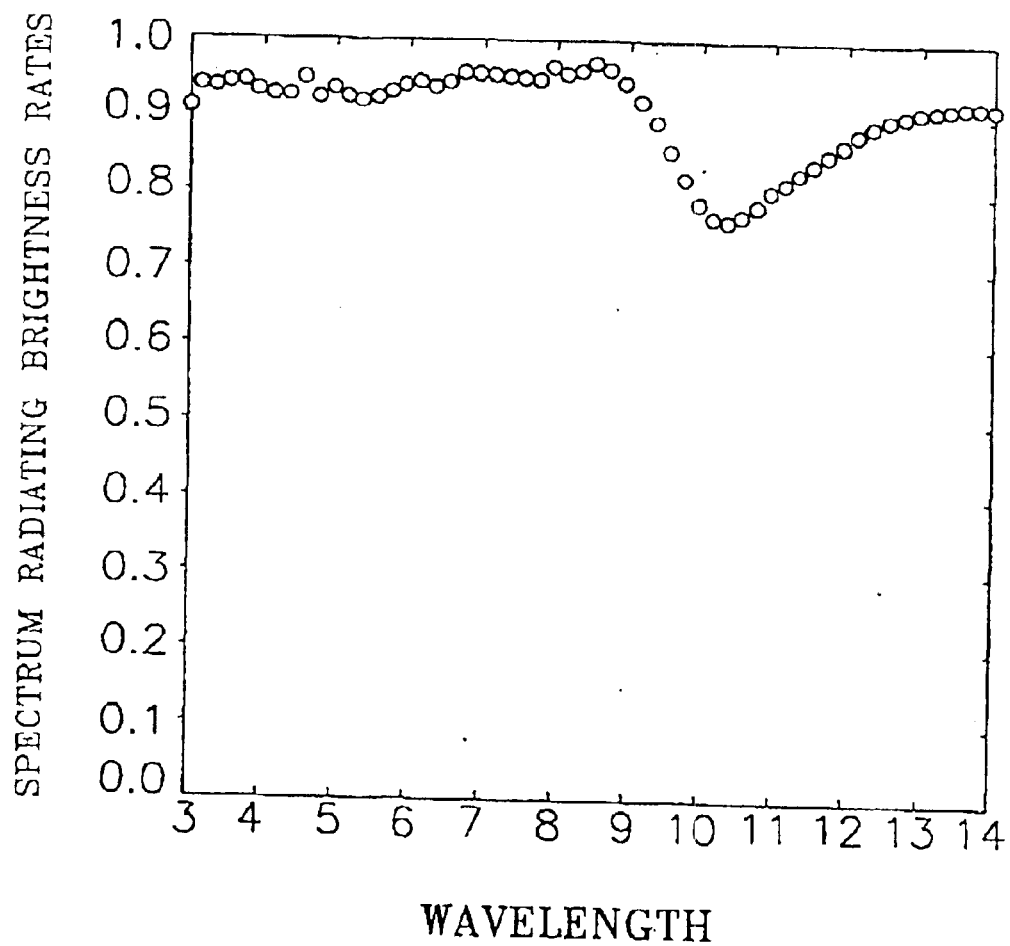
FIG. 1 is a graph for illustrating far infrared ray spectrum radiating rates depending upon changes in wavelength ($\mu$m) of the far infrared ray radiating glass product manufactured by a method (i)

Hereinafter, the present invention will be described in detail.

An illuminating glass product of the present invention is manufactured with far infrared ray radiating glass into a bulb or a glass diffuser, for instance, by mixing a far infrared ray radiating matter into a general glass forming material.

A glass material, generally used for manufacturing glass, such as silicon-dioxide ($SiO_2$), sodium carbonate ($Na_2CO_3$), limestone ($CaCo_3$), aluminum hydroxide ($Al(OH)_3$), potassium carbonate ($K_2CO_3$) or the like is finely ground into powder, or any of the aforementioned materials can be used as it is.

A variety of materials like germanium, jade, ceramic and the like can be used as a far infrared ray radiating matter (A). Among these materials, jade is most preferred due to a certain level of its transparency, a characteristic required to be an illustrating glass product. Jade radiates far infrared rays close to 90–95% at room temperature and close to 100% by heating. Jade is a general term for jadeite and nephrite, and jadeite is harder than nephrite, greater in the degree of strength. Jadeite has the chemical structure of $NaAlSi_2O_6$, belonging to a group of rare stones, with a hardness of 7, while nephrite has the chemical structure of $Ca_2(Mg,Fe)_5Si_8O_{22}(OH)_2$, a medium component of tremolite and actinolite, belonging to a group of amphibole, with a hardness of 6 or 6.5. Particularly, nephrite is a fibrous material, consisting of an aggregate of numerous hairlike crystals and fine particles, containing minerals, calcium, magnesium, the elements essentially required for human body, identical to main components of human body, so that it is very beneficial for human body to make contacts with those elements that emit powerful far infrared rays. In addition, differently from a granular type of jadeite, nephrite is made of fine particles, so that nephrite may be more suitable for production of glass goods.

A far infrared ray radiating matter (for instance: nephrite) used for the far infrared ray radiating glass product of the present invention is finely ground into about 320–325 mesh. The far infrared ray radiating matter can be directly mixed (i) with a glass manufacturing powder, or can be coated (ii) onto a pre-made glass plate. The far infrared ray radiating glass product of the present invention can be generally made into a bulb by the first method (i), or into a glass diffuser by the latter method (ii). On the contrary, a colored bulb and a glass diffuser have been often used for interior decorations in recent years, without any limitation to application methods.

Now, an illuminating glass product of the present invention will be described about its structure and its manufacturing method. First of all, a material (B) to be used generally manufacturing glass such as silicon dioxide $SiO_2$, sodium carbonate $Na_2CO_3$, limestone $CaCo_3$, aluminum hydroxide $Al(OH)_3$, potassium carbonate $K_2CO_3$ or the like is finely ground, and a far infrared ray radiating matter (A), nephrite, are separately ground into fine powders in 320–325 mesh. Then, the separately ground powders (A and B) are mixed at the approximate weight percentage ratio of 10–1:90–99, and the mixture is heated and liquefied in a melting pot at 1300–1350 degrees centigrade or so. The liquid type of the mixture is injected into a desired shape of a mold (for instance: electric bulb or glass diffuser), and the liquid type of the mold cools off into an illuminating glass product having the far infrared ray radiating function with loss of internal stress.

At this time, if the weight percentage of the nephrite powder to the glass manufacturing material is greater than 10, there may be deformation or cracks in the glass product. If the weight percentage of the nephrite powder is less than 1% weight percentage to the glass manufacturing material powder, the far infrared ray radiating efficiency gets lower.

On the other hand, a second method (ii) for manufacturing an illuminating glass product will be described in accordance with the present invention. At this time, a predetermined shape of a glass plate should be pre-manufactured and ready for use. The far infrared ray radiating matter (for instance: nephrite) is finely ground into a particle size of about 320–325 mesh, mixed with a pigment at the weight percentage rate of 10–1%, and coated onto the glass plate with a silk net of 300–325 mesh by a silk printing method. Accordingly, this glass plate is dried and solidified by using an electric furnace at about 650 centigrade degrees to prevent the far infrared ray radiating matter from peeling off.

Preferred Embodiment

Table 1 shows results of far infrared ray spectrum radiation rates and spectrum radiation brightness rates of the far infrared ray radiating glass product made by the latter method (ii) depending upon changes in wavelength.

TABLE 1

| WAVE-LENGTH (μm) | SPECTRUM RADIATION RATE | SPECTRUM RADIATION BRIGHTNESS W/(cm$^3$ · μm · sr) |
| --- | --- | --- |
| 3.000 | 0.970 | 1.295e−3 |
| 4.000 | 0.933 | 4.094e−3 |
| 5.000 | 0.895 | 7.455e−3 |
| 6.000 | 0.928 | 6.231e−3 |
| 7.000 | 0.927 | 7.344e−3 |
| 8.000 | 0.922 | 6.633e−3 |
| 9.000 | 0.706 | 4.417e−3 |
| 9.600 | 0.626 | 3.554e−3 |
| 10.000 | 0.689 | 3.660e−3 |
| 11.000 | 0.789 | 3.518e−3 |
| 12.000 | 0.849 | 3.164e−3 |
| 13.000 | 0.837 | 2.603e−3 |
| 14.000 | 0.851 | 2.214e−3 |

Table 1 shows results of a test obtained by Korea standardization research institute (No: 00-10403-002, date: Apr. 10, 2000, name: far infrared ray spectrum radiation rates). The test was set up at atmosphere temperature of 23±1° C. and relative humidity of 50% and conducted at the well-maintained temperature of 183° C. to measure radiation energy per area and per hour. As a result of the test conducted at the wavelength range of 3–14 μm, the radiating glass of the present invention shows spectrum radiation rates at the minimum of 61.2%, to the maximum of 97%.

If the far infrared ray radiating glass product of the present invention is. used as a bulb or reflecting shade, the aforementioned heating condition can be satisfied with a filament of the bulb. Therefore, it can be assumed that the present invention achieved a high efficiency of far infrared ray radiation rates, about 61.2–97%.

Table 2 shows far infrared ray spectrum radiation rates and spectrum radiation brightness rates of the far infrared ray radiating glass product made by the first method (i) depending upon changes in wavelength.

TABLE 2

| WAVE-LENGTH (μm) | SPECTRUM RADIATION RATE | SPECTRUM RADIATION BRIGHTNESS W/(cm$^3$ · μm · sr) |
| --- | --- | --- |
| 3.000 | 0.912 | 2.625e−3 |
| 4.000 | 0.933 | 7.289e−3 |
| 5.000 | 0.936 | 1.035e−3 |
| 6.000 | 0.941 | 1.113e−3 |
| 7.000 | 0.958 | 1.059e−3 |
| 8.000 | 0.967 | 9.348e−3 |
| 8.600 | 0.973 | 8.511e−3 |
| 9.000 | 0.948 | 7.733e−3 |
| 9.600 | 0.860 | 6.282e−3 |
| 10.000 | 0.790 | 5.348e−3 |
| 10.200 | 0.773 | 5.025e−3 |
| 11.000 | 0.806 | 4.494e−3 |
| 12.000 | 0.869 | 3.987e−3 |
| 13.000 | 0.911 | 3.447e−3 |
| 14.000 | 0.921 | 2.887e−3 |

Table 2 shows results of a test obtained under the same conditions as those for Table 1 except the measurement temperature of 219° C. The test was conducted by Korea standardization research institute (No: 00-10403-002, date: Apr. 10, 2000, name: far infrared ray spectrum radiation rates). As a result of the test conducted at the wavelength range of 3–14 μm, the far infrared ray radiating glass product of the present invention shows spectrum radiation rates, the minimum of 77.2% to the maximum of 97.3%.

Figure 2:
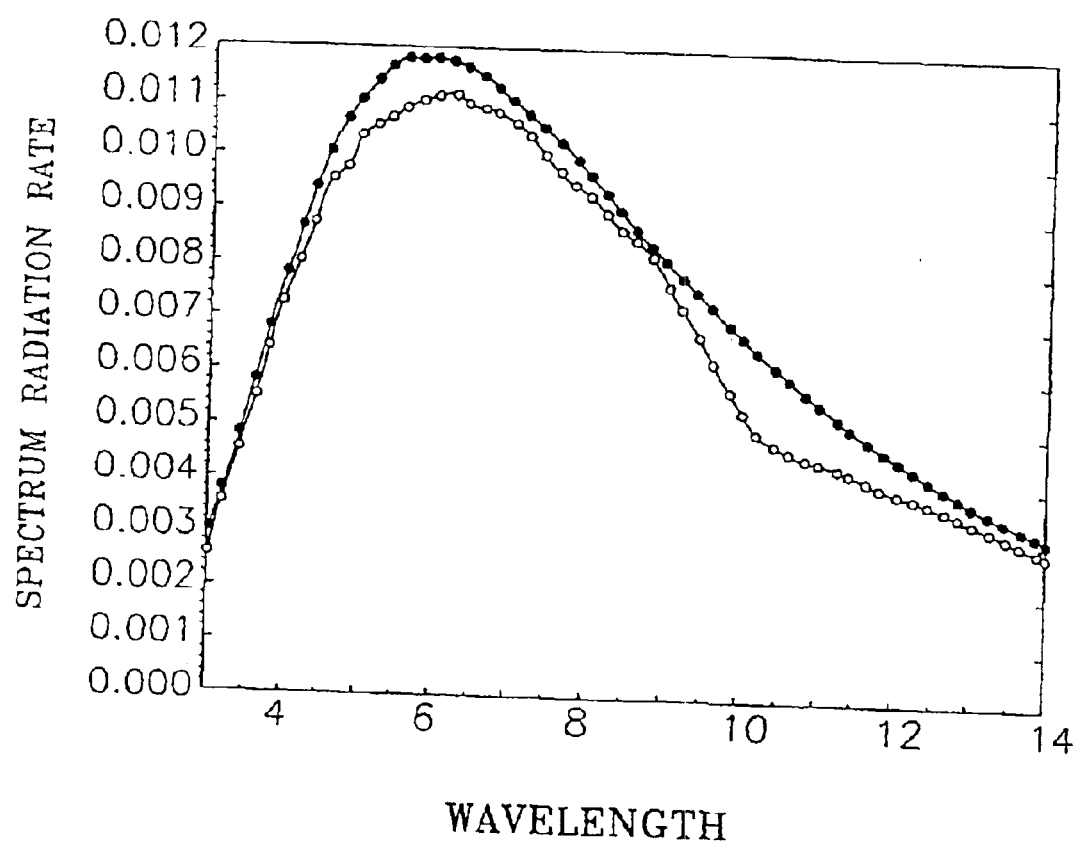
FIG. 2 is a graph for illustrating far infrared ray spectrum radiating brightness rates {W/(cm2. $\mu$m. sr)} depending upon changes in wavelength ($\mu$m) of the far infrared ray radiating glass product manufactured by a method (i).

Such results are illustrated in FIGS. 1 and 2. Particularly, in FIG. 2, the line marked in white dots are measurements with glass, while the line marked in black dots are spectrum radiation brightness rates of a black body at the aforementioned temperature.

According to the results, if the far infrared ray radiating glass of the present invention is used as a bulb or glass diffuser, the aforementioned heating condition can be met with a filament of the bulb. Therefore, it can be assumed that the present invention achieved a high efficiency of far infrared ray radiation rates, about 80–97%.

Industrial Use

As described above, as long as the illuminating glass product of the present invention has its bulb kept on, the filament of the bulb is heated to achieve a superior effect for a high efficiency of far infrared ray radiation rates by manipulation of a simple illuminating apparatus with additional heating means. With such glass products having an far infrared ray radiating function, it would be possible to use them as an illuminating lamp in surgery and patient recovery rooms to reinforce treatment and recovery effects, in pens for cattle and pigs or fish farming facilities to enhance their growth by radiation of far infrared rays, or in study rooms and offices to raise efficiency of work or study. Besides, the far infrared ray radiating glass product can also be applied as an illuminating apparatus to ripening of fermented food to thereby shorten ripening time of the fermented food through activation of fermenting enzymes or for bathrooms to relieve fatigue through activation of metabolism in a human body.

What is claimed is:

1. A bulb glass made of a fused mixture of a glass material at a weight percentage of 90–99 and a nephrite [$Ca_2(Mg, Fe)_5Si_8O_{22}(OH)_2$] at a weight percentage of 10–1 wherein the glass material comprising powder of silicon dioxide ($SiO_2$) sodium carbonate ($Na_2CO_3$), lime stone ($CaCO_3$), aluminum hydroxide ($Al(OH)_3$) and potassium carbonate ($K_2CO_3$), and the nephrite being powder of 320–325 mesh.

2. A method for manufacturing a bulb glass, the method comprising the steps of:

manufacturing a glass material powder comprising silicon dioxide ($SiO_2$) sodium carbonate ($Na_2CO_3$), lime stone ($CaCO_3$), aluminum hydroxide ($Al((OH)_3$) and potassium carbonate ($K_2CO_3$);

manufacturing nephrite [$Ca_2(Mg, Fe)_5Si_8O_{22}(OH)_2$] powder of 320–325 mesh;

mixing and stirring the glass material powder at a weight percentage of 90–99 and the nephrite powder it a weight percentage of 10–1;

liquefying the powder mixture at a temperature of 1300 through 1350 centigrade degrees; and cooling off the liquid mixture in a bulb-shaped meld.

* * * * *